US011636340B2

(12) United States Patent
Liu et al.

(10) Patent No.: US 11,636,340 B2
(45) Date of Patent: Apr. 25, 2023

(54) MODELING METHOD AND APPARATUS FOR DIAGNOSING OPHTHALMIC DISEASE BASED ON ARTIFICIAL INTELLIGENCE, AND STORAGE MEDIUM (71) Applicants: BGI SHENZHEN, Guangdong (CN); EYE, EAR, NOSE, AND THROAT HOSPITAL OF FUDAN UNIVERSITY, Shanghai (CN)

(72) Inventors: Xiaoqing Liu, Shenzhen (CN); Jiaxu Hong, Shanghai (CN); Yong Ni, Shenzhen (CN); Shuangshuang Li, Shenzhen (CN); Lili Wang, Shenzhen (CN); Wei He, Shenzhen (CN); Youwen Guo, Shenzhen (CN); Yuxuan Liu, Shenzhen (CN); Yong Liu, Shenzhen (CN); Wei Wang, Shenzhen (CN); Ruiqi Xu, Shenzhen (CN); Jingyi Cheng, Shanghai (CN); Lijia Tian, Shanghai (CN); Wenbin Chen, Shenzhen (CN); Xun Xu, Shenzhen (CN)

(73) Assignees: BGI SHENZHEN, Shenzhen (CN); EYE, EAR, NOSE, AND THROAT HOSPITAL OF FUDAN UNIVERSITY, Shanghai (CN)

(*) Notice: Subject to any disclaimer, the term of this patent is extended or adjusted under 35 U.S.C. 154(b) by 381 days.

(21) Appl. No.: 16/967,087

(22) PCT Filed: Apr. 17, 2018

(86) PCT No.: PCT/CN2018/083393
§ 371 (c)(1),
(2) Date: Aug. 3, 2020

(87) PCT Pub. No.: WO2019/200535
PCT Pub. Date: Oct. 24, 2019

(65) Prior Publication Data
US 2021/0035689 A1 Feb. 4, 2021

(51) Int. Cl.
G06N 3/08 (2023.01)
G16H 50/20 (2018.01)
(Continued)

(52) U.S. Cl.
CPC ............ *G06N 3/08* (2013.01); *A61B 3/12* (2013.01); *A61B 3/14* (2013.01); *G06F 18/214* (2023.01);
(Continued)

(58) Field of Classification Search
CPC ........ G16H 10/20; G16H 20/10; G16H 20/30; G16H 70/60; G16H 50/20
(Continued)

(56) References Cited

U.S. PATENT DOCUMENTS

2016/0292856 A1 10/2016 Niemeijer et al.
2019/0204620 A1* 7/2019 Bonnin .................. G02C 7/061
2020/0160999 A1* 5/2020 Rim ...................... A61B 3/1176

FOREIGN PATENT DOCUMENTS

CN 106682389 A 5/2017
CN 106709254 A 5/2017
(Continued)

OTHER PUBLICATIONS

International Search Report issued for PCT/CN2018/083393, dated Jan. 7, 2019.
(Continued)

Primary Examiner — Ajibola A Akinyemi
(74) Attorney, Agent, or Firm — Westman, Champlin & Koehler, P.A.; Z. Peter Sawicki; Amanda M. Prose (57) ABSTRACT The present disclosure proposes a modeling method and apparatus for diagnosing an ophthalmic disease based on
(Continued)

artificial intelligence, and a storage medium. The modeling method includes: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

18 Claims, 5 Drawing Sheets

(51) Int. Cl.
| | | |
|---|---|---|
| *G16H 10/20* | (2018.01) | |
| *A61B 3/12* | (2006.01) | |
| *A61B 3/14* | (2006.01) | |
| *G06T 7/00* | (2017.01) | |
| *G06F 18/214* | (2023.01) | |
| *G06F 18/21* | (2023.01) | |
| *G06V 10/764* | (2022.01) | |
| *G06V 10/80* | (2022.01) | |
| *G06V 10/82* | (2022.01) | |
| *G06V 20/69* | (2022.01) | |

(52) U.S. Cl.
CPC ........ *G06F 18/2178* (2023.01); *G06T 7/0012* (2013.01); *G06V 10/764* (2022.01); *G06V 10/80* (2022.01); *G06V 10/82* (2022.01); *G06V 20/698* (2022.01); *G16H 10/20* (2018.01); *G16H 50/20* (2018.01); *G06T 2207/20081* (2013.01); *G06T 2207/20084* (2013.01)

(58) Field of Classification Search
USPC ........................................................ 382/128
See application file for complete search history.

(56) References Cited

FOREIGN PATENT DOCUMENTS

| | | |
|---|---|---|
| CN | 107358606 A | 11/2017 |
| CN | 107437092 A | 12/2017 |
| CN | 107680683 A | 2/2018 |
| CN | 107909621 A | 4/2018 |
| EP | 3065086 A1 | 9/2016 |

OTHER PUBLICATIONS

Written Opinion issued for PCT/CN2018/083393, dated Jan. 7, 2019.

* cited by examiner

MODELING METHOD AND APPARATUS FOR DIAGNOSING OPHTHALMIC DISEASE BASED ON ARTIFICIAL INTELLIGENCE, AND STORAGE MEDIUM

CROSS-REFERENCE TO RELATED APPLICATION

This application is a US national phase application of International Application No. PCT/CN2018/083393, filed on Apr. 17, 2018, the entire contents of which are incorporated herein by reference.

FIELD

The present disclosure mainly relates to a field of medical technologies, and more particularly to a modeling method and apparatus for diagnosing an ophthalmic disease based on artificial intelligence, and a storage medium.

BACKGROUND

With application of artificial intelligence in a medical field, more and more medical diagnosis cases employ a medical diagnosis method based on the artificial intelligence. Relying on an image recognition and depth learning technology, the artificial intelligence may better solve problems that may exist in the medical field when image large data is manually processed. As a branch of a clinical specialty, modeling for diagnosing an ophthalmic disease focuses on eyes, which are only body surface organs in a human body in addition to skin. 60-70 percent of the ophthalmic diseases may be diagnosed through image information. A combination of the artificial intelligence and medical images makes a better breakthrough for ophthalmology.

Modeling for diagnosing the ophthalmic disease based on the artificial intelligence in the related art is oriented to differential diagnosis of a single disease, which is still quite different from an actual situation of modeling for diagnosing numerous possibilities of ophthalmic diseases which a patient and a doctor may face in clinical practice, and diagnosis effect for the ophthalmic disease is not good.

SUMMARY

The present disclosure aims to solve one of the technical problems in the related art to at least some extent.

For this, a first objective of the present disclosure is to provide a modeling method for diagnosing an ophthalmic disease based on artificial intelligence.

Another objective of the present disclosure is to provide a modeling apparatus for diagnosing an ophthalmic disease based on artificial intelligence.

Another objective of the present disclosure is to provide a non-transitory computer readable storage medium.

To achieve the above objectives, a first aspect of embodiments of the present disclosure provides a modeling method for diagnosing an ophthalmic disease based on artificial intelligence. The modeling method includes: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

To achieve the above objectives, a second aspect of embodiments of the present disclosure provides a modeling apparatus for diagnosing an ophthalmic disease based on artificial intelligence. The apparatus includes a processor and a memory. The memory is configured to store executable program codes. The processor is configured to operate a program corresponding to the executable program codes by reading the executable program codes stored in the memory to perform: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

To achieve the above objectives, embodiments of the present disclosure provide a non-transitory computer readable storage medium. The storage medium is configured to store an application. The application, when executed, is configured to execute a modeling method for diagnosing the ophthalmic disease based on artificial intelligence. The method may include: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

Additional aspects and advantages of embodiments of the present disclosure will be given in part in the following descriptions, and become apparent in part from the following descriptions, or be learned from the practice of the embodiments of the present disclosure.

BRIEF DESCRIPTION OF THE DRAWINGS

The above and/or additional aspects and advantages of the present disclosure will become apparent and more readily appreciated from the following descriptions made for embodiments with reference to the accompanying drawings, in which.

DETAILED DESCRIPTION

Description will be made in detail below to embodiments of the present disclosure. Examples of embodiments are illustrated in the accompanying drawings, in which, the same or similar numbers represent the same or similar elements or elements with the same or similar functions. Embodiments described below with reference to the accompanying drawings are exemplary, which are intended to explain the present disclosure and do not be understood a limitation of the present disclosure. On the contrary, embodiments of the present disclosure include all changes, modifications and equivalents that fall within the spirit and scope of the appended claims.

In the related art, with application of artificial intelligence in a medical field, more and more medical diagnosis cases employ a medical diagnosis method based on the artificial intelligence. Relying on an image recognition and depth learning technology, the artificial intelligence may better solve problems that may exist in the medical field when image large data is manually processed. As a branch of a clinical specialty, modeling for diagnosing an ophthalmic disease focuses on eyes, which are only body surface organs in a human body in addition to skin. 60-70 percent of the ophthalmic diseases may be diagnosed through image information. A combination of the artificial intelligence and medical images makes a better breakthrough for ophthalmology. Modeling for diagnosing the ophthalmic disease based on the artificial intelligence in the related art is oriented to differential diagnosis of a single disease, which is still quite different from an actual situation of modeling for diagnosing numerous possibilities of ophthalmic diseases which a patient and a doctor may face in clinical practice, and diagnosis effect for the ophthalmic disease is not good.

Therefore, embodiments of the present disclosure provide a modeling method for diagnosing an ophthalmic disease based on artificial intelligence. Multi-dimensional data collections are constructed, that is, a data collection of ophthalmic images and a data collection of non-image ophthalmic disease diagnosis questionnaires are established. The non-image ophthalmic disease diagnosis questionnaires comprehensively consider symptom information of an ophthalmic disease of a patient and personal information of the patient. Moreover, with embodiments of the present disclosure, two classification models are configured and trained, different models are respectively trained based on data with different features, a first classification model and a second classification model subjected to the training are merged, such that clinic, ophthalmic images and the personal information of the patients are integrated to assist the ophthalmic diagnosis, and an artificial intelligence technology may better assist modeling for diagnosing the ophthalmic disease, thereby effectively improving intelligence and accuracy of modeling for diagnosing all kinds of ophthalmic diseases, and improving diagnosis effect.

Figure 1:
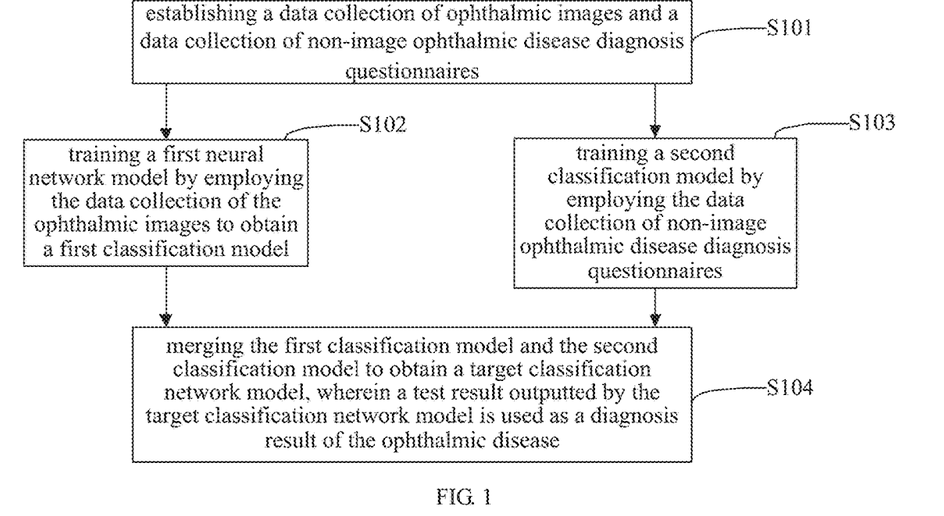
FIG. 1 is a flow chart illustrating a modeling method for diagnosing an ophthalmic disease based on artificial intelligence according to an embodiment of the present disclosure.

FIG. 1 is a flow chart illustrating a modeling method for diagnosing an ophthalmic disease based on artificial intelligence according to an embodiment of the present disclosure.

Referring to FIG. 1, the method includes followings.

At block S101, a data collection of ophthalmic images and a data collection of non-image ophthalmic disease diagnosis questionnaires are established.

The data collection of the ophthalmic images is a data collection related to images collected from eyes of patients, which may include, for example, clinical data of the images of eyes of the patients and a public data collection related to the images of the eyes, which is not limited thereto.

In detail, the data collection of the ophthalmic images may include fundus grayscale images and markers of target features in the fundus grayscale images. For example, the target feature may be a macular feature or a fundus vascular feature, which is not limited thereto.

The data collection of the non-image ophthalmic disease diagnosis questionnaires is information that the doctor selects from inquiry information of the patients based on ophthalmic diagnosis experience, which has a reference value to model for diagnosing the ophthalmic disease, for example, includes symptom information of the ophthalmic diseases and personal information of the patient.

Alternatively, the symptom information of the ophthalmic diseases includes at least one of: red eye information, eye dryness information, eye pain information, eye itch information, foreign body sensation information, burning sensation information, photophobia information, and tears information, which is not limited thereto. The personal information of the patients includes at least one of: age, gender, infection progress, and high-risk factors, which is not limited thereto.

With embodiments of the present disclosure, during training the model, the above common symptom information of the ophthalmic diseases and the personal information of the patients are comprehensively considered, which may reduce consumption of model calculation resources while ensuring accuracy of modeling for diagnosing the ophthalmic disease, and improve diagnosis efficiency from another dimension. Furthermore, embodiments of the present disclosure may also be expanded on the basis of the above information, and the method is flexible, thereby implementing that a dimension of model parameters meets a personalized diagnosis requirement of actual clinic.

It should be understood that, the symptom information of the ophthalmic diseases may be various symptoms in actual clinical diagnosis, and the personal information of the patient may also be situations of various patients in the actual clinical diagnosis, which are not limited to the above. For example, the symptom information of the ophthalmic diseases may also be amblyopia information and hyperopia information, and the personal information of the patients may also be, such as, drug allergy information.

In a detailed example, the age in the personal information of the patients may be divided into four stages: junior (0~18 years old), young (19~40 years old), middle age (40~60 years old) and senile (over 60 years old). The infection progress may include, such as, acute, chronic, persistent, or repeated disease. The high-risk factor may include, such as, hypertension, diabetes, ocular trauma, familial inheritance, viral infection, immune diseases, etc., and in combination with the symptom information of the ophthalmic diseases, a total of 37-dimension factors exist.

With embodiments of the present disclosure, in a detailed performing procedure, initial ophthalmic image data may be enhanced by employing an image preprocessing algorithm. The image preprocessing algorithm includes at least one of: an algorithm for randomly deforming an image, an algorithm for shearing an image, and an algorithm for compensating a color or brightness of an image. Then, image simulation data corresponding to enhanced ophthalmic image data is generated as the data collection of the ophthalmic images, and the data collection of the non-image ophthalmic disease diagnosis questionnaires is extracted from an inquiry condition.

The initial ophthalmic image data may be a fundus image of the patient.

Examples of the image preprocessing algorithm may include:

rotation/reflection: rotating an image randomly within a certain angle or changing an orientation of an image content;

flipping: flipping an image horizontally or vertically;

zooming: enlarging or reducing an image based on a certain proportion;

shifting: shifting an image in a certain way on an image plane, and specifying a shifting range and a shifting step in a random or artificially defined way, and shifting the image along a horizontal or vertical direction to change a position of the image content;

scaling: zooming in or out the image based on a specified scale factor, or referring to a feature extraction idea of the shifting, utilizing the specified scale factor to filter the image to construct a scale space and changing a size or a blur degree of the image content;

contrast transformation: in a HSV (hue, saturation, value) color space of an image, changing the saturation S and the value V, keeping the hue H unchanged, and performing exponential operation (an exponential factor is between 0.25 and 4) on the saturation S and the value V of each pixel to increase an illumination change; and noise disturbance: randomly disturbing each pixel RGB (red, green, blue) of an image, in which common noise modes are salt and pepper noise and Gaussian noise.

Figure 2A:
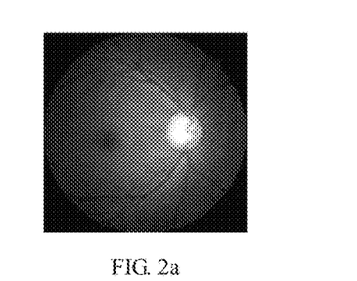
FIG. 2a is a schematic diagram illustrating initial ophthalmic image data according to embodiments of the present disclosure.
Figure 2B:
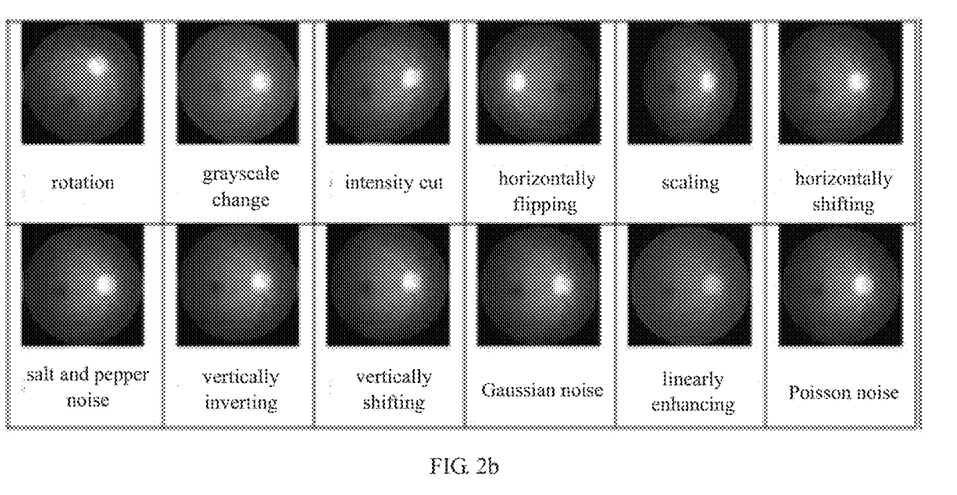
FIG. 2b is a schematic diagram illustrating enhanced ophthalmic image data according to embodiments of the present disclosure.

Referring to FIG. 2, FIG. 2a is a schematic diagram illustrating initial ophthalmic image data according to embodiments of the present disclosure. FIG. 2b is a schematic diagram illustrating enhanced ophthalmic image data according to embodiments of the present disclosure. The enhanced ophthalmic image data includes: a rotated ophthalmic image, an ophthalmic image subjected to a grayscale change, an ophthalmic image subjected to an intensity cut, a horizontally flipped ophthalmic image, a scaled ophthalmic image, a horizontally shifted ophthalmic image, an ophthalmic image added with the salt and pepper noise, a vertically inverted ophthalmic image, a vertically shifted ophthalmic image, an ophthalmic image added with the Gaussian noise, a linearly enhanced ophthalmic image, an ophthalmic image added with Poisson noise.

Alternatively, with embodiments of the present disclosure, in a detailed performing procedure, a target feature in the initial ophthalmic image data is segmented to obtain the enhanced ophthalmic image data. The target feature is a fundus vascular feature or a macular feature.

For example, feature enhancement may be performed by means of target detection and image semantic segmentation. Taking performing semantic segmentation on the image of the eye by a U-net network as an example, the U-net network is an encoder-decoder structure. The encoder gradually reduces spatial dimensions of a pooling layer, and the decoder gradually repairs details and spatial dimensions of an object. There is usually a quick connection between the encoder and the decoder, which may help the decoder repair details of the target feature better.

Figure 3A:
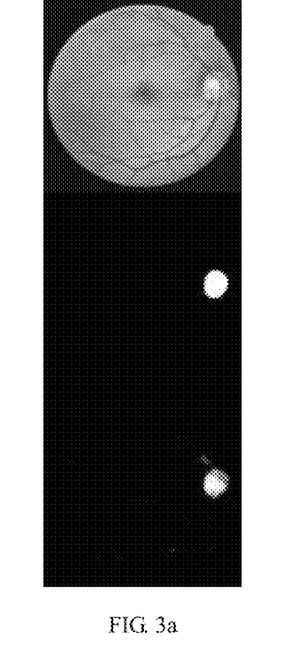
FIG. 3a is a schematic diagram illustrating a macular feature according to embodiments of the present disclosure.
Figure 3B:
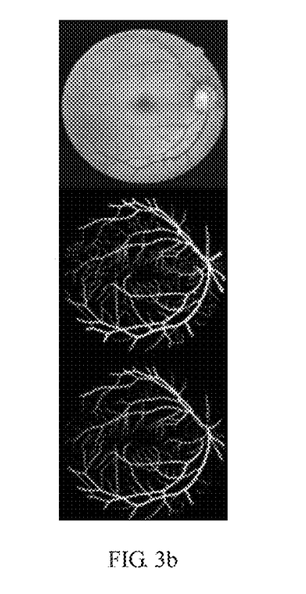
FIG. 3b is a schematic diagram illustrating a fundus vascular feature according to embodiments of the present disclosure.

Referring to FIG. 3a, FIG. 3a is a schematic diagram illustrating a macular feature according to embodiments of the present disclosure. FIG. 3b is a schematic diagram illustrating a fundus vascular feature according to embodiments of the present disclosure. By segmenting the target feature in the initial ophthalmic image data, the feature in the initial ophthalmic image data may be enhanced, such that feature parameters in the data collection of the ophthalmic images are more obvious, thereby improving accuracy of modeling for diagnosing the ophthalmic disease. FIG. 3a is divided into upper, middle and lower rows. The upper row includes a fundus grayscale image, the middle row includes a marker of the target feature (macular feature) in the fundus grayscale image, and the lower row is an enhanced macular feature. FIG. 3b is divided into upper, middle and lower rows. The upper row includes a fundus grayscale image, the middle row includes a marker of the target feature (fundus vascular feature) in the fundus grayscale image, and the lower row is an enhanced fundus vascular feature.

With embodiments of the present disclosure, in a detailed performing procedure, a generative adversarial network may also be employed to generate the image simulation data corresponding to the enhanced ophthalmic image data as the data collection of the ophthalmic images.

As an example, in embodiments of the present disclosure, a deep convolutional generative adversarial network (DC-GAN) may be employed to generate the image simulation data corresponding to the enhanced ophthalmic image data. The DCGAN is a better model combined by a convolutional neural network and an adversarial network.

Figure 4:
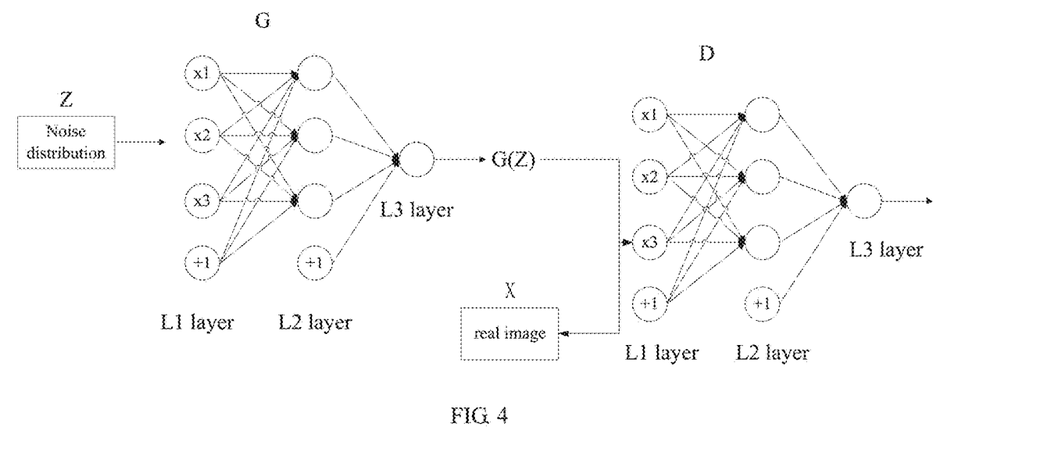
FIG. 4 is a schematic diagram illustrating a generative adversarial network model.

Referring to FIG. 4, FIG. 4 is a schematic diagram illustrating a generative adversarial network model. The generative adversarial network model is combined by a discrimination model and a generation model. Z represents noise, i.e., input of G, which may be Gaussian noise and generally uniform noise. Fake image G(z) is generated after G. The G(z) and x are taken as inputs of D. The output of D represents a possibility that the data is real, which ranges from 0-1.

In embodiments of the present disclosure, the image simulation data corresponding to the enhanced ophthalmic image data is generated as the data collection of the ophthalmic images by employing the generative adversarial network, which may quantify input data for model training and is convenient for calculation. The depth network model in the artificial intelligence is combined with the data collection of the ophthalmic images to realize aided diagnosis based on the artificial intelligence.

In addition, in embodiments of the present disclosure, in order to ensure a reference value of the data collection of the ophthalmic images, before the depth network model is trained, some data synthesis algorithms may also be employed, to generate more data of the ophthalmic images by utilizing existed data of the ophthalmic images, which may effectively enrich the data collection for model training.

With embodiments of the present disclosure, in a detailed performing procedure, a data synthesis algorithm in the related art may be employed, such as a synthetic minority oversampling technique (SMOTE) algorithm, to generate more data of the ophthalmic images.

With embodiments of the present disclosure, in a detailed performing procedure, imbalance of the data collection of the ophthalmic images may also be optimized. For example, a sampling method may be employed. The sampling method may include an over sampling and an under sampling. The sampling method may add slight random disturbance to a newly generated data collection of the ophthalmic images, and combine an EasyEnsemble sampling method and a BalanceCascade sampling method to train the data collection of the ophthalmic images to optimize the processing for data imbalance.

At block S102, a first neural network model is trained by employing the data collection of the ophthalmic images to obtain a first classification model.

At block S103, a second classification model is trained by employing the data collection of non-image ophthalmic disease diagnosis questionnaires.

Procedures for actions at blocks S102 and S103 may refer to following embodiments.

At block S104, the first classification model and the second classification model are merged to obtain a target classification network model. A test result outputted by the target classification network model is used as a diagnosis result of the ophthalmic disease.

Alternatively, in some embodiments, in a detailed performing procedure, a part of the convolution layers in the first classification model as a network feature and a feature of the second classification model are respectively intercepted, the network feature and the feature of the second classification model are merged by employing a dense connection network or a batch normalization technology to obtain a merged feature, and the target classification network model is trained and obtained by employing the merged feature.

In this embodiment, the multi-dimensional data collections are constructed, that is, the data collection of the ophthalmic images and the data collection of the non-image ophthalmic disease diagnosis questionnaires are established, the two classification models respectively are configured and trained, different models are respectively trained based on the data with different features, and the first classification model and the second classification model subjected to the training are merged, such that the clinic, and the ophthalmic images and the personal information of the patients are integrated to assist the ophthalmic diagnosis, and the artificial intelligence technology may better assist modeling for diagnosing the ophthalmic disease, thereby effectively improving the intelligence and accuracy of modeling for diagnosing the all kinds of ophthalmic diseases, and improving the diagnosis effect.

Figure 5:
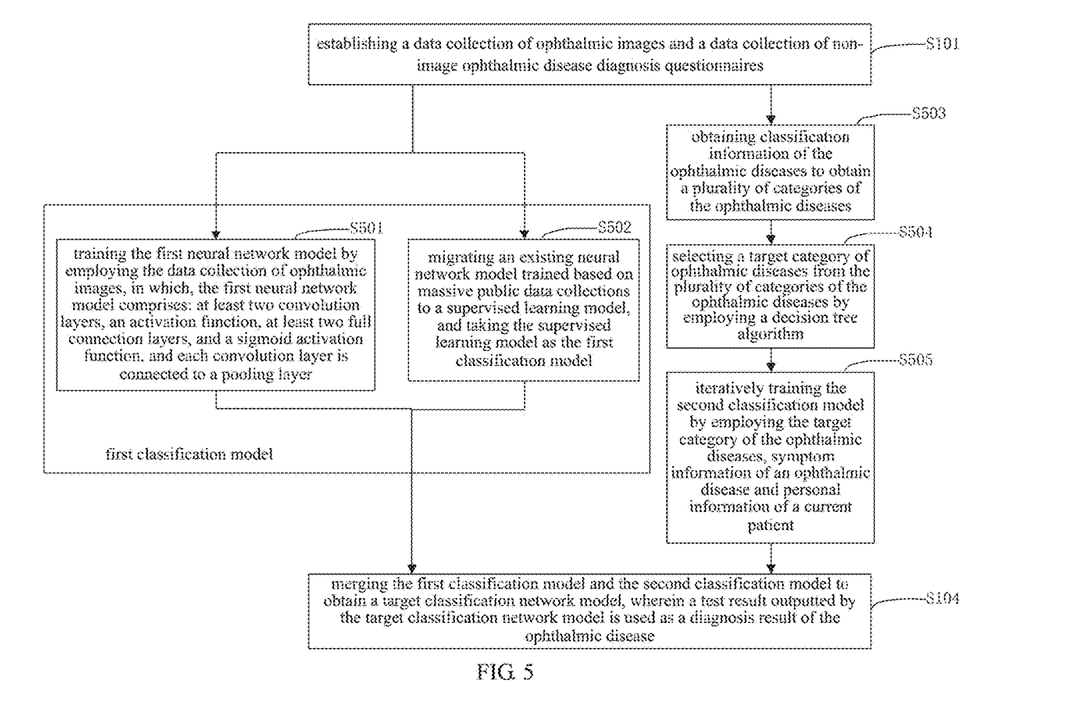
FIG. 5 is a flow chart illustrating a modeling method for diagnosing an ophthalmic disease based on artificial intelligence according to another embodiment of the present disclosure.

Alternatively, in some embodiments, as another example, referring to FIG. 5, FIG. 5 is a flow chart illustrating a modeling method for diagnosing an ophthalmic disease based on artificial intelligence according to another embodiment of the present disclosure. The actions at block S102 in the above embodiment may include followings.

At block S501, the first neural network model is trained by employing the data collection of ophthalmic images. The first neural network model includes: at least two convolution layers, an activation function, at least two full connection layers, and a sigmoid activation function. Each convolution layer is connected to a pooling layer.

At block S502, an existing neural network model trained based on massive public data collections is migrated to a supervised learning model, and the supervised learning model is taken as the first classification model.

In embodiments of the present disclosure, the first classification model may be obtained by respectively employing actions at block S501 or S502, or may be obtained by combining the actions at blocks S501 and S502, which is not limited thereto.

In a detailed performing procedure, firstly, the first neural network model may be trained by employing the data collection of the ophthalmic images. The first neural network model includes: the at least two convolution layers, the activation function, the at least two full connection layers, and the sigmoid activation function. Each convolution layer is connected to a pooling layer. Then, the existing neural network model trained based on the massive public data collections is migrated to the supervised learning model. In detail, the existing neural network model (such as a VGG16 model, a VGG19 model, a Resnet50 model, an InceptionV3 model) trained based on the massive public data collections may be migrated to the supervised learning model. According to the present disclosure, a migration learning model is used for migration, such that a result learned from the data collection of the ophthalmic images under a condition of sufficient data quantity may be migrated to a model with small required data quantity, and calculation resource consumption of the model may be reduced while training accuracy of the model is ensured.

As an example, embodiments of the present disclosure provide a detailed performing method for migrating the existing neural network model trained based on the massive public data collections to the supervised learning model, of which detailed description may refer followings.

In a first example, a bottleneck feature of the first neural network model is learned. A convolution layer of the existing neural network model is utilized, and then a model of the convolution layer is trained based on the collected data collection of the ophthalmic images. Output of the trained model of the convolution layer is taken as the bottleneck feature, and the bottleneck feature is recorded. Then one supervised learning model is trained independently based on the collected data collection of the ophthalmic images. The supervised learning model may be, such as, a support vector machine (SVM), an XGBoost (extreme gradient Boosting), or a fully connected neural network.

Referring to Table 1, Table 1 illustrates accuracy results of a model trained by migrating and learning the existing neural network model VGG19 to the supervised learning model XGBoost. The data collection of the ophthalmic images used in the training procedure is 2844 anterior segment images and 2595 fundus original images. Categories of the ophthalmic diseases corresponding to the data collection of the ophthalmic images are: 1169 cataract cases, 1328 corneal cases, 865 retinal cases, 865 glaucoma cases, and non-ocular normal images. In the training procedure, 80% images in the data collection of the ophthalmic images are randomly used for model training, and the remaining 20% images in the data collection of the ophthalmic images are used for model evaluation. As illustrated in Table 1, for each of four common ophthalmic diseases including cataract, corn, glaucoma and retina, the accuracy of the model before and after the migration is relatively close, and the accuracy is close to or more than 90%. A data amount is greatly reduced after the migration, thereby improving prediction efficiency of the model.

TABLE 1

|  | AUC | Accuracy |
| --- | --- | --- |
| Cataract | 0.880 | 0.875 |
| Corn | 0.985 | 0.929 |
| Glaucoma | 0.957 | 0.890 |
| Retina | 0.955 | 0.899 |

The AUC in Table 1 represents an area under the curve. The greater the AUC value, the higher the accuracy of a classification model. The AUC value ranges from 0 to 1. When the AUC value is 1, the classification model corresponding to the AUC value is a classification model with the best accuracy.

Figure 6:
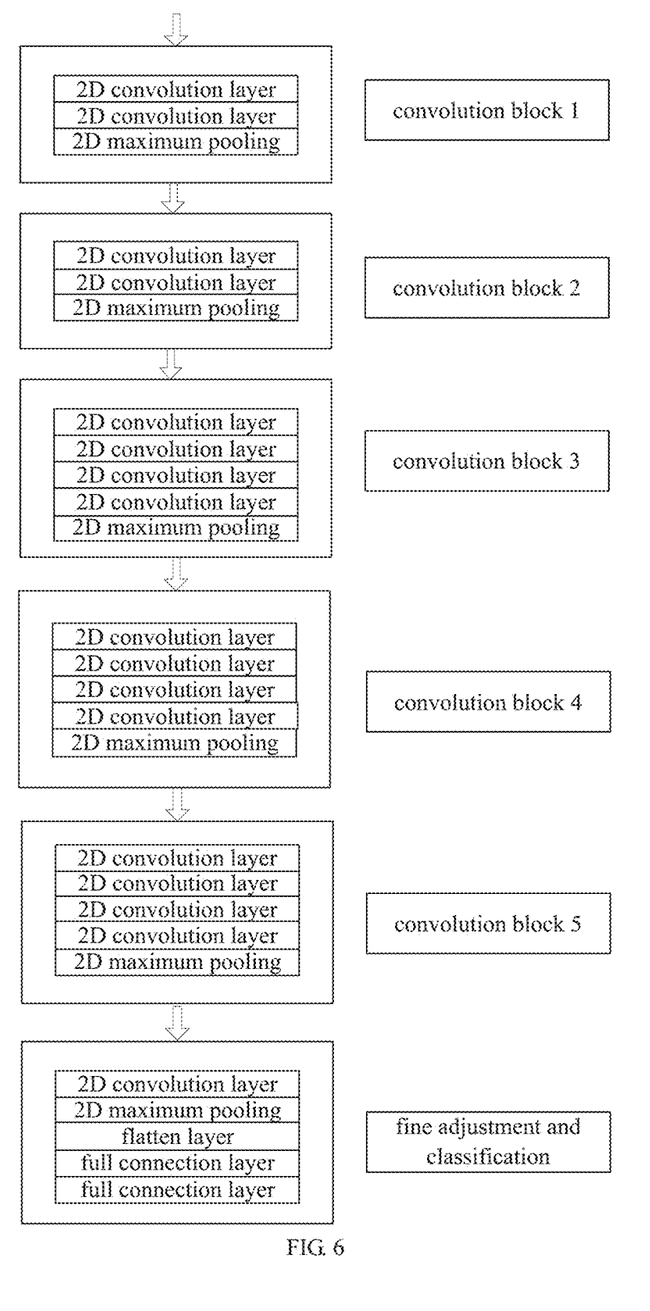
FIG. 6 is a schematic diagram illustrating a fine adjustment procedure according to embodiments of the present disclosure.

Further, in order to further improve the accuracy of the above model, in embodiments of the present disclosure, fine adjustment may be appropriately performed on the existing neural network model VGG19 based on a size of a training data collection. Referring to FIG. 6, FIG. 6 is a schematic diagram illustrating a fine adjustment procedure according to embodiments of the present disclosure.

(1) The neural network model VGG19 is constructed, a preset weight is loaded.

(2) A preset full connection network is added to a top of the neural network model VGG19 and the above preset weight is loaded.

(3) A part of parameters of the neural network model VGG19 are frozen.

For example, referring to FIG. 6, parameters of the convolution layers (convolution blocks 1 to 5) before a last convolution layer may be frozen, and then the neural network model VGG19 subjected to the fine adjustment may be trained based on the data collection of the ophthalmic images. By properly performing the fine adjustment on the existing neural network model, adequacy of the migration and learning may be effectively improved.

Based on same data as Table 1, Table 2 illustrates accuracy results of the neural network model VGG19 subjected to the migration and the fine adjustment. As illustrated in Table 2, for the four common ophthalmic diseases, all the accuracies are close to or more than 90%.

TABLE 2

|  | AUC | Accuracy |
| --- | --- | --- |
| Cataract | 0.907 | 0.882 |
| Corn | 0.989 | 0.946 |
| Glaucoma | 0.938 | 0.861 |
| Retina | 0.954 | 0.907 |

In a second example, embodiments of the present disclosure may also migrate the existing neural network model trained based on the massive public data collections to the supervised learning model by employing a multitasking learning mechanism. By employing the multitasking learning mechanism, the efficiency of modeling for diagnosing the ophthalmic disease may be effectively improved.

Table 3 illustrates migrated accuracy results based on the multitasking learning mechanism. For the four common ophthalmic diseases, the model performs well with all the accuracies approaching or exceeding 90%.

TABLE 3

|  | AUC | Accuracy |
| --- | --- | --- |
| Cataract | 0.947 | 0.876 |
| Corn | 0.986 | 0.948 |
| Glaucoma | 0.927 | 0.885 |
| Retina | 0.917 | 0.859 |

In a third example, referring to Table 4, this embodiment employs a mixed double-model solution. One network model is on a basis of the neural network model VGG19, a final convolution layer of the neural network model VGG19 is intercepted to. The other network model is a ResNet50 model, and a final convolution layer of the ResNet50 model is intercepted to. Then a feature of the neural network model VGG19 and a feature of the ResNet50 model are merged, and a merged feature is employed to train a part of convolution layers, to obtain a target classification network model.

As illustrated in Table 4, compared to a single model, a model mixed by the two models may improve the AUC or accuracy of diagnosing the ophthalmic diseases such as the cataract, the corn and the glaucoma to some extent.

TABLE 4

|  | AUC | Accuracy |
| --- | --- | --- |
| Cataract | 0.936 | 0.882 |
| Corn | 0.991 | 0.958 |
| Glaucoma | 0.938 | 0.879 |
| Retina | 0.943 | 0.867 |

The action at block S103 in the above embodiment may also include followings.

At block S503, classification information of the ophthalmic diseases is obtained to obtain a plurality of categories of the ophthalmic diseases.

With embodiments of the present disclosure, in a performing procedure, common ophthalmic diseases may be divided into 17 categories based on broad categories, and each broad category of ophthalmic diseases may be divided into a plurality of minor categories of ophthalmic diseases. There are 127 minor categories in all. Each minor ophthalmic disease has its corresponding common symptom information, high-risk individuals, high-risk age stages, infection progress, and high-risk factors.

Therefore, for the above symptom information of the ophthalmic diseases and the personal information of the patients, each minor ophthalmic disease may be described using 37-dimension features.

At block S504, a target category of ophthalmic diseases is selected from the plurality of categories of the ophthalmic diseases by employing a decision tree algorithm.

The target category of the ophthalmic diseases is ophthalmic diseases matched to symptom information of an ophthalmic disease of a current patient and personal information of the current patient in combination with an actual condition.

The actual condition may be, for example, a disease $A_k$ always appears on a certain factor, but the current patient does not appear this factor. For example, a senile cataract always occurs in an elderly group, and a possibility of the senile cataract is completely excluded when the current patient is young. Therefore, there may be excluded a category of the ophthalmic diseases of the senile cataract in the elderly group, and the above target category of the ophthalmic diseases may fall in the remaining categories of the ophthalmic diseases.

As another example, a certain factor appears on the current patient, but the disease $A_k$ does not appear the certain factor. For example, the current patient appears black shadow fluttering in the eye, but vernal keratoconjunctivitis does not have the symptom, so there is excluded a possibility of the current patient suffering from a category of the ophthalmic diseases of the vernal keratoconjunctivitis. Therefore, the category of the ophthalmic diseases of the vernal keratoconjunctivitis may be excluded, and remaining categories of the ophthalmic diseases may be taken as the above target category of the ophthalmic diseases.

At block S505, the second classification model is iteratively trained by employing the target category of the ophthalmic diseases, the symptom information of the ophthalmic disease and the personal information of the current patient.

The second classification model is configured to analyze the symptom information of the ophthalmic disease and the personal information of the current patient based on match information of each category of ophthalmic diseases with the current patient.

A calculation method of the second classification model may be described as follows.

For the target category of the ophthalmic diseases, a match value between a current patient B and each category of the ophthalmic diseases $A_i$ may be calculated, the match values are arranged in a descending order, and categories of ophthalmic diseases with the top five match values are taken as actual prediction results of the ophthalmic disease of the current patient B. A formula for calculating the matching value may adopt Hamming distance and is represented as:

$$1 - \frac{1}{n}\sum_{j=0}^{j=n-1} w_j(A_{ij} - B_j),$$

where, n=37 and corresponds to 37—dimension features of each category of the ophthalmic diseases, and a set criteria of a weight $w_j$ is illustrated in Table 5 below.

TABLE 5

| Case condition | Weight $w_j$ |
|---|---|
| Ophthalmic disease $A_i$ may appear a feature $F_i$, and the tested case has the feature. | 1.0 |
| Ophthalmic disease $A_i$ may appear a feature $F_i$, the tested case does not have the feature. | <1.0 |

With this embodiment, the second classification model is trained in the above way, and patients with 120 kinds of ophthalmic diseases are tested. If an actual ophthalmic disease diagnosed for the patient is included in the predicted five categories of the ophthalmic diseases, the prediction result is deemed correct, and an accuracy rate of a final test result is 91%.

Figure 7:
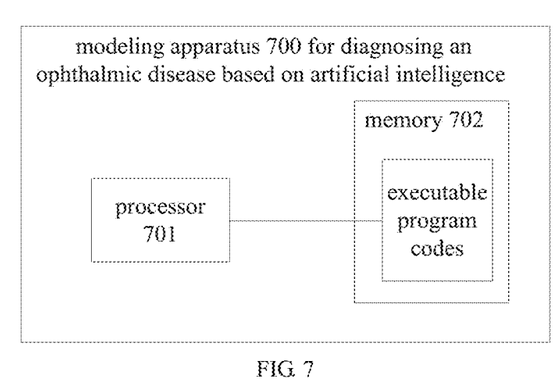
FIG. 7 is a block diagram illustrating a modeling apparatus for diagnosing an ophthalmic disease based on artificial intelligence according to an embodiment of the present disclosure.

FIG. 7 is a block diagram illustrating a modeling apparatus for diagnosing an ophthalmic disease based on artificial intelligence according to an embodiment of the present disclosure.

Referring to FIG. 7, the apparatus includes: a processor 701 and a memory 702. The memory 702 is configured to store executable program codes by the processor. The processor 701 is configured to operate a program corresponding to the executable program codes by reading the executable program codes stored in the memory 702 to perform: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

Alternatively, in some embodiments, the processor 701 is also configured to: train the first neural network model by employing the data collection of ophthalmic images, in which, the first neural network model includes: at least two convolution layers, an activation function, at least two full connection layers, and a sigmoid activation function, and each convolution layer is connected to a pooling layer; migrate an existing neural network model trained based on massive public data collections to a supervised learning model, and taking the supervised learning model as the first classification model.

Alternatively, in some embodiments, the processor 701 is also configured to: perform fine adjustment on parameters of the convolution layers in the first neural network model, and training the first neural network model subjected to the fine adjustment by employing the data collection of the ophthalmic images; and migrating the existing neural network model trained based on the massive public data collections to the supervised learning model includes: migrating the first neural network model obtained after the fine adjustment to the supervised learning model.

Alternatively, in some embodiments, the processor 701 is also configured to: migrate the existing neural network model trained based on the massive public data collections to the supervised learning model by employing a multitasking learning mechanism.

Alternatively, in some embodiments, the processor 701 is also configured to: respectively intercept a part of the convolution layers in the first classification model as a network feature and a feature of the second classification model; merge the network feature and the feature of the second classification model by employing a dense connection network or a batch normalization technology to obtain a merged feature, and train and obtain the target classification network model by employing the merged feature.

Alternatively, in some embodiments, the processor 701 is also configured to: enhance initial ophthalmic image data by employing an image preprocessing algorithm, the image preprocessing algorithm including at least one of: an algorithm for randomly deforming an image, an algorithm for shearing an image, and an algorithm for compensating a color or brightness of an image; generate image simulation data corresponding to enhanced ophthalmic image data as the data collection of the ophthalmic images; and extract the data collection of the non-image ophthalmic disease diagnosis questionnaires from an interrogation condition.

Alternatively, in some embodiments, the processor 701 is also configured to: generate the image simulation data corresponding to the enhanced ophthalmic image data as the data collection of the ophthalmic images by employing a generative adversarial network.

Alternatively, in some embodiments, the data collection of non-image ophthalmic disease diagnosis questionnaires comprises: symptom information of the ophthalmic diseases and personal information of patients, and the processor 701 is also configured to: obtain classification information of the ophthalmic diseases to obtain a plurality of categories of the ophthalmic diseases; select a target category of ophthalmic diseases from the plurality of categories of the ophthalmic diseases by employing a decision tree algorithm; and iteratively train the second classification model by employing the target category of the ophthalmic diseases, symptom information an ophthalmic disease and the personal information of a current patient, in which, the second classification model is configured to analyze the symptom information of the ophthalmic disease and the personal information of a current patient based on match information of each category of ophthalmic diseases.

Alternatively, in some embodiments, the processor 701 is also configured to: segment a target feature in the initial ophthalmic image data to obtain the enhanced ophthalmic image data, wherein the target feature is a fundus vascular feature or a macular feature.

It should be noted that description for the modeling method for diagnosing the ophthalmic disease based on artificial intelligence according to the above embodiments illustrated in FIG. 1-FIG. 6 is also applicable to the modeling apparatus for diagnosing the ophthalmic disease based on artificial intelligence according to this embodiment, and implementation principles are similar, which are not elaborated herein.

In this embodiment, multi-dimensional data collections are constructed, that is, the data collection of the ophthalmic images and the data collection of non-image ophthalmic disease diagnosis questionnaires, the two classification models are respectively configured and trained, different models are respectively trained based on data with different features, and the first classification model and the second classification model subjected to the training are merged, such that the clinic, the ophthalmic images and the personal information of the patients are integrated to assist the ophthalmic diagnosis, and the artificial intelligence technology may better assist modeling for diagnosing the ophthalmic disease, thereby effectively improving the intelligence and accuracy of modeling for diagnosing all the kinds of ophthalmic diseases, and improving the diagnosis effect.

To achieve the above embodiments, the present disclosure also provides a storage medium. The storage medium is configured to store an application. The application, when executed, is configured to execute the modeling method for diagnosing the ophthalmic disease based on artificial intelligence according to this embodiment of the present disclosure. The method includes: establishing a data collection of ophthalmic images and a data collection of non-image ophthalmic disease diagnosis questionnaires; training a first neural network model by employing the data collection of the ophthalmic images to obtain a first classification model; training a second classification model by employing the data collection of non-image ophthalmic disease diagnosis questionnaires; and merging the first classification model and the second classification model to obtain a target classification network model, in which, a test result outputted by the target classification network model is used as a diagnosis result of the ophthalmic disease.

It should be noted that, the principle and the implementation of the application for executing the modeling method for diagnosing the ophthalmic disease based on artificial intelligence according to this embodiment is similar as the modeling method for diagnosing the ophthalmic disease based on artificial intelligence according to the above embodiments, which are not elaborated herein in order to avoid redundancy.

With the storage medium according to embodiments of the present disclosure, multi-dimensional data collections are constructed, that is, the data collection of the ophthalmic images and the data collection of non-image ophthalmic disease diagnosis questionnaires, the two classification models are respectively configured and trained, different models are respectively trained based on data with different features, and the first classification model and the second classification model subjected to the training are merged, such that the clinic, the ophthalmic images and the personal information of the patients are integrated to assist the ophthalmic diagnosis, and the artificial intelligence technology may better assist modeling for diagnosing the ophthalmic disease, thereby effectively improving the intelligence and accuracy of modeling for diagnosing all the kinds of ophthalmic diseases, and improving the diagnosis effect.

It should be noted that, in the description of the present disclosure, the terms "first", "second" and the like are only for description purpose, and it cannot be understood as indicating or implying its relative importance. In addition, in the description of the present disclosure, the term "a plurality of" means two or more, unless specified otherwise.

Any procedure or method described in a flow chart or described herein in other ways may be understood to include one or more modules, segments or portions of codes of executable instructions for achieving specific logical functions or steps in the procedure, and the scope of a preferred embodiment of the present disclosure includes other implementations. The order of execution is different from that which is depicted or discussed, including executing functions in a substantially simultaneous manner or in an opposite order according to the related functions, which should be understood by those skilled in the art which embodiments of the present disclosure belong to.

It should be understood that each part of the present disclosure may be realized by the hardware, software, firmware or their combination. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

Those skilled in the art shall understand that all or parts of the steps in the above embodiment method of the present disclosure may be achieved by commanding the related hardware with a program. The program may be stored in a computer readable storage medium, and the program includes one or a combination of the steps in the method embodiments of the present disclosure when run on a computer.

In addition, each function unit of the embodiments of the present disclosure may be integrated in a processing module, or these units may be separate physical existence, or two or more cells are integrated in a processing module. The integrated module may be realized in a form of hardware or in a form of software function modules. When the integrated module is realized in the form of software function module and is sold or used as a standalone product, the integrated module may be stored in a computer readable storage medium.

The storage medium mentioned above may be a read-only memory, a magnetic disk or CD, etc.

In the description of the present disclosure, reference throughout this specification to "an embodiment," "some embodiments," "an example," "a specific example," or "some examples," means that a particular feature, structure, material or feature described in connection with the embodiment or example is included in at least one embodiment or example of the present disclosure. The appearances of the above phrases throughout this specification are not necessarily referring to the same embodiment or example. Furthermore, the particular feature, structure, material or feature may be combined in any suitable manner in one or more embodiments or examples.

Although embodiments of the present disclosure have been shown and described above, it should be understood that the above-mentioned embodiments are exemplary and should not be construed as limiting the present disclosure. The skilled in the art can make changes, modifications, substitutions and variations to the above-mentioned embodiments within the scope of the present disclosure.

What is claimed is:

1. A modeling method for diagnosing an ophthalmic disease based on artificial intelligence, comprising:
    establishing a data collection of ophthalmic images and a data collection of non-image ophthalmic disease diagnosis questionnaires;
    training a first neural network model by employing the data collection of the ophthalmic images to obtain a first classification model;
    training a second classification model by employing the data collection of non-image ophthalmic disease diagnosis questionnaires; and
    merging the first classification model and the second classification model to obtain a target classification network model, wherein a test result outputted by the target classification network model is used as a diagnosis result of the ophthalmic disease,
    wherein training the first neural network model by employing the data collection of the ophthalmic images to obtain the first classification model comprises at least one of:
    training the first neural network model by employing the data collection of ophthalmic images, in which, the first neural network model comprises: at least two convolution layers, an activation function, at least two full connection layers, and a sigmoid activation function, and each convolution layer is connected to a pooling layer; and
    migrating an existing neural network model trained based on massive public data collections to a supervised learning model, and taking the supervised learning model as the first classification model.

2. The method of claim 1, wherein after training the first neural network model by employing the data collection of the ophthalmic images, the method further comprises:
    performing fine adjustment on parameters of the convolution layers in the first neural network model, and training the first neural network model subjected to the fine adjustment by employing the data collection of the ophthalmic images; and
    migrating the existing neural network model trained based on the massive public data collections to the supervised learning model comprises:
    migrating the first neural network model subjected to the fine adjustment to the supervised learning model.

3. The method of claim 2, wherein migrating the existing neural network model trained based on the massive public data collections to the supervised learning model comprises:
    migrating the existing neural network model trained based on the massive public data collections to the supervised learning model by employing a multitasking learning mechanism.

4. The method of claim 1, wherein migrating the existing neural network model trained based on the massive public data collections to the supervised learning model comprises:
    migrating the existing neural network model trained based on the massive public data collections to the supervised learning model by employing a multitasking learning mechanism.

5. The method of claim 1, wherein merging the first classification model and the second classification model to obtain the target classification network model comprises:
    respectively intercepting a part of the convolution layers in the first classification model as a network feature and a feature of the second classification model;
    merging the network feature and the feature of the second classification model by employing a dense connection network or a batch normalization technology to obtain a merged feature, and training and obtaining the target classification network model by employing the merged feature.

6. The method of claim 1, wherein establishing the data collection of the ophthalmic images and the data collection of the non-image ophthalmic disease diagnosis questionnaires comprises:
    enhancing initial ophthalmic image data by employing an image preprocessing algorithm, the image preprocessing algorithm comprising at least one of: an algorithm for randomly deforming an image, an algorithm for shearing an image, and an algorithm for compensating a color or brightness of an image;
    generating image simulation data corresponding to enhanced ophthalmic image data as the data collection of the ophthalmic images; and
    extracting the data collection of the non-image ophthalmic disease diagnosis questionnaires from an interrogation condition.

7. The method of claim 6, wherein enhancing the initial ophthalmic image data by employing the image preprocessing algorithm further comprises:
    segmenting a target feature in the initial ophthalmic image data to obtain the enhanced ophthalmic image data, wherein the target feature is a fundus vascular feature or a macular feature.

8. The method of claim 6, wherein the data collection of the non-image ophthalmic disease diagnosis questionnaires comprises: symptom information of the ophthalmic diseases and personal information of patients, and training the second classification model by employing the data collection of the non-image ophthalmic disease diagnosis questionnaires comprises:
    obtaining classification information of the ophthalmic diseases to obtain a plurality of categories of the ophthalmic diseases;
    selecting a target category of ophthalmic diseases from the plurality of categories of the ophthalmic diseases by employing a decision tree algorithm; and
    iteratively training the second classification model by employing the target category of the ophthalmic diseases, symptom information of an ophthalmic disease and personal information of a current patient, in which, the second classification model is configured to analyze the symptom information of the ophthalmic disease and the personal information of the current patient based on match information of each category of ophthalmic diseases.

9. The method of claim 6, wherein generating the image simulation data corresponding to the ophthalmic image data enhanced as the data collection of the ophthalmic images comprises:
generating the image simulation data corresponding to the enhanced ophthalmic image data as the data collection of the ophthalmic images by employing a generative adversarial network.

10. The method of claim 1, wherein the data collection of the non-image ophthalmic disease diagnosis questionnaires comprises: symptom information of the ophthalmic diseases and personal information of patients, and training the second classification model by employing the data collection of the non-image ophthalmic disease diagnosis questionnaires comprises:
obtaining classification information of the ophthalmic diseases to obtain a plurality of categories of the ophthalmic diseases;
selecting a target category of ophthalmic diseases from the plurality of categories of the ophthalmic diseases by employing a decision tree algorithm; and
iteratively training the second classification model by employing the target category of the ophthalmic diseases, symptom information of an ophthalmic disease and personal information of a current patient,
in which, the second classification model is configured to analyze the symptom information of the ophthalmic disease and the personal information of the current patient based on match information of each category of ophthalmic diseases.

11. The method of claim 10, wherein the symptom information of the ophthalmic disease comprises at least one of: red eye information, eye dryness information, eye pain information, eye itch information, foreign body sensation information, burning sensation information, photophobia information, and tears information.

12. The method of claim 10, wherein the personal information of the patients comprises at least one of: age, gender, infection progress, and high-risk factors.

13. A modeling apparatus for diagnosing an ophthalmic disease based on artificial intelligence, comprising:
a processor; and
a memory, configured to store executable program codes by the processor;
wherein the processor is configured to operate a program corresponding to the executable program codes by reading the executable program codes stored in the memory to perform:
establishing a data collection of ophthalmic images and a data collection of non-image ophthalmic disease diagnosis questionnaires;
training a first neural network model by employing the data collection of the ophthalmic images to obtain a first classification model;
training a second classification model by employing the data collection of non-image ophthalmic disease diagnosis questionnaires; and
merging the first classification model and the second classification model to obtain a target classification network model, wherein a test result outputted by the target classification network model is used as a diagnosis result of the ophthalmic disease, wherein the processor is further configured to perform at least one of:
training the first neural network model by employing the data collection of ophthalmic images, in which, the first neural network model comprises: at least two convolution layers, an activation function, at least two full connection layers, and a sigmoid activation function, and each convolution layer is connected to a pooling layer; and
migrating an existing neural network model trained based on massive public data collections to a supervised learning model, and taking the supervised learning model as the first classification model.

14. The apparatus of claim 13, wherein the processor is further configured to:
perform fine adjustment on parameters of the convolution layers in the first neural network model, and training the first neural network model subjected to the fine adjustment by employing the data collection of the ophthalmic images; and
the processor migrates the existing neural network model trained based on the massive public data collections to the supervised learning model by performing:
migrating the first neural network model subjected to the fine adjustment to the supervised learning model.

15. The apparatus of claim 13, wherein the processor is further configured to:
migrate the existing neural network model trained based on the massive public data collections to the supervised learning model by employing a multitasking learning mechanism.

16. The apparatus of claim 13, wherein the processor is further configured to:
respectively intercept a part of the convolution layers in the first classification model as a network feature and a feature of the second classification model;
merge the network feature and the feature of the second classification model by employing a dense connection network or a batch normalization technology to obtain a merged feature, and train and obtain the target classification network model by employing the merged feature.

17. The apparatus of claim 13, wherein the processor is further configured to:
enhance initial ophthalmic image data by employing an image preprocessing algorithm, the image preprocessing algorithm comprising at least one of: an algorithm for randomly deforming an image, an algorithm for shearing an image, and an algorithm for compensating a color or brightness of an image;
generate image simulation data corresponding to enhanced ophthalmic image data as the data collection of the ophthalmic images; and
extract the data collection of the non-image ophthalmic disease diagnosis questionnaires from an interrogation condition.

18. A non-transitory computer readable storage medium having instructions stored thereon, wherein when the instruction is executed by a processor of an electronic device, the processor is configured to execute a modeling method for diagnosing the ophthalmic disease based on artificial intelligence, and the method comprises:
establishing a data collection of ophthalmic images and a data collection of non-image ophthalmic disease diagnosis questionnaires;

training a first neural network model by employing the data collection of the ophthalmic images to obtain a first classification model;

training a second classification model by employing the data collection of non-image ophthalmic disease diagnosis questionnaires; and merging the first classification model and the second classification model to obtain a target classification network model, wherein a test result outputted by the target classification network model is used as a diagnosis result of the ophthalmic disease, wherein training the first neural network model by employing the data collection of the ophthalmic images to obtain the first classification model comprises at least one of:

training the first neural network model by employing the data collection of ophthalmic images, in which, the first neural network model comprises: at least two convolution layers, an activation function, at least two full connection layers, and a sigmoid activation function, and each convolution layer is connected to a pooling layer; and migrating an existing neural network model trained based on massive public data collections to a supervised learning model, and taking the supervised learning model as the first classification model.

* * * * *